United States Patent
Kramer et al.

(10) Patent No.: US 10,967,294 B1
(45) Date of Patent: *Apr. 6, 2021

(54) ENRICHED ROOT POWDER PRODUCTS AND METHODS OF PRODUCING THEREOF

(71) Applicant: ThermoLife International, LLC, Phoenix, AZ (US)

(72) Inventors: Ronald Kramer, Phoenix, AZ (US); Alexandros Nikolaidis, Nea Kallikratia (GR)

(73) Assignee: ThermoLife International, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/893,309

(22) Filed: Jun. 4, 2020

Related U.S. Application Data

(63) Continuation of application No. 16/130,952, filed on Sep. 13, 2018, now Pat. No. 10,702,796.

(60) Provisional application No. 62/558,113, filed on Sep. 13, 2017.

(51) Int. Cl.
| | |
|---|---|
| *B01D 11/02* | (2006.01) |
| *A61K 36/21* | (2006.01) |
| *A61K 36/18* | (2006.01) |
| *A23L 5/30* | (2016.01) |
| *A61K 36/185* | (2006.01) |
| *A23L 5/20* | (2016.01) |

(52) U.S. Cl.
CPC .......... *B01D 11/0288* (2013.01); *A23L 5/23* (2016.08); *A23L 5/30* (2016.08); *A61K 36/185* (2013.01); *A61K 36/21* (2013.01); *A61K 2236/19* (2013.01); *A61K 2236/333* (2013.01); *A61K 2236/51* (2013.01); *A61K 2236/53* (2013.01); *B01D 11/0257* (2013.01)

(58) Field of Classification Search
CPC . B01D 11/0288; B01D 11/0257; B01D 11/02; B01D 11/028; B01D 17/08; B01D 17/085; B01D 17/10; B01D 17/12; B01D 36/00; B01D 36/003; B01D 36/008; B01D 61/04; B01D 61/10; B01D 2221/06; B01D 2311/04; B01D 2311/2688; B01D 2311/2673; A61K 36/185; A61K 36/21; A61K 2236/333; A61K 2236/19; A61K 2236/53; A61K 2236/51; A61K 2236/10; A61K 2236/33; A61K 2236/50; A23L 5/21; A23L 5/23; A23L 5/25; A23L 5/30
USPC ....... 210/631, 632, 634, 651, 767, 770, 774, 210/806; 426/7, 49, 425, 429, 489, 495, 426/615
See application file for complete search history.

(56) References Cited

U.S. PATENT DOCUMENTS

| | | | | |
|---|---|---|---|---|
| 1,452,739 | A * | 4/1923 | Hood | C13B 20/005 127/55 |
| 1,511,472 | A * | 10/1924 | Clark | C13B 20/02 127/55 |
| 1,533,033 | A * | 4/1925 | Sauer | C13B 20/02 127/48 |
| 1,887,050 | A | 11/1932 | Vierling | |
| 2,342,162 | A | 2/1944 | Musher | |
| 3,249,512 | A | 5/1966 | Bode | |
| 4,026,977 | A * | 5/1977 | Bourganel | B01D 67/0011 264/41 |
| 4,238,567 | A | 12/1980 | Staron | |
| 5,213,836 | A | 5/1993 | McGillivray | |
| 5,413,928 | A | 5/1995 | Weathers | |
| 5,486,474 | A | 1/1996 | Bradley | |
| 2003/0036565 | A1 | 2/2003 | Parkin | |
| 2005/0274469 | A1 | 12/2005 | Lundberg | |
| 2010/0076050 | A1 | 3/2010 | Pietrzkowski | |
| 2010/0310714 | A1 | 12/2010 | Lotter | |
| 2011/0313042 | A1* | 12/2011 | Kramer | A61P 21/00 514/565 |
| 2011/0313043 | A1* | 12/2011 | Kramer | C07D 233/64 514/565 |
| 2013/0071371 | A1 | 3/2013 | Bryan | |
| 2015/0366901 | A1* | 12/2015 | Chirinos | A61P 9/04 424/718 |
| 2016/0038533 | A1 | 2/2016 | Bryan | |
| 2016/0353782 | A1 | 8/2016 | Ruppman | |
| 2018/0133247 | A1* | 5/2018 | Green | A61K 9/0095 |
| 2018/0263944 | A1* | 9/2018 | Tripp | A61P 13/12 |
| 2020/0078428 | A1* | 3/2020 | Noguchi | A61K 45/06 |
| 2020/0300424 | A1* | 9/2020 | Chami | F21V 23/06 |

OTHER PUBLICATIONS

Publication entitled "Study confirms OxyStorm benefit", downloaded from https://www.ingredientsnetwork.com/study-confirms-oxystorm-benefit-news043894.html, Nov. 25, 2016. (Year: 2016).*
Catalog entitled "Oxystorm", downloaded from https://www.plthealth.com/product-catalog/oxystorm/, available on-line 2016. (Year: 2016).*
Jurgen Wruss et al. "Compositional characteristics of commercial beetroot products and beetroot juice prepared from seven beetroot varieties grown in Upper Austria", Journal of Food Composition and Analysis, vol. 42, 2015—pp. 46-55, p. 52, table 4, p. 53, tables 5-6.
Iltaf Shah et al. "Determination of Nitrate and Nitrite Content of Dietary Supplements Using Ion Chromatography", Journal of Analytical & Bioanalytical Techniques, 2013.
Gavin Van De Walle, "Sports Nutrition Supplements: Formulatingwith Nitrate Salts vs. Beetroot", published on Nov. 3, 2017, pp. 1-5. (Year: 2017).
"Nitrate in vegetables Scientific Opinion of the Panel on Contaminants in the Food Chain", (Question No. EFSA-Q-2006-071), The EFSA Journal (Published Apr. 10, 2008), vol. 689, pp. 1-79. (Year: 2008).

(Continued)

*Primary Examiner* — Joseph W Drodge
(74) *Attorney, Agent, or Firm* — Booth Udall Fuller, PLC

(57) ABSTRACT

The present disclosure relates to methods of enriching beetroot products to increase the nitrate content of the beetroot powder product. The disclosure also relates to beetroot powder products with increased with at least 4% nitrate.

27 Claims, No Drawings

(56) References Cited

OTHER PUBLICATIONS

What is in your Beet Juice? Nitrate and Nitrite Content of Beet Juice Products Marketed to Athletes, published in International Journal of Sport Nutrition and Exercise Metabolism, Published 2019, vol. 29, pp. 345-349. (Year: 2019).

Keller et al., "Dietary nitrate and nitrite concentrations in food patterns and dietary supplements", Nutrition Today, vol. 00, No. 0, pp. 1-9. (2017).

* cited by examiner

ENRICHED ROOT POWDER PRODUCTS AND METHODS OF PRODUCING THEREOF

CROSS-REFERENCE TO RELATED APPLICATIONS

This application is a continuation application of the earlier and pending U.S. Utility Patent Application to Ronald Kramer, et. al., titled "Amino Acid Compositions," application Ser. No. 16/309,952, filed Sep. 13, 2018, which claims the benefit of U.S. Provisional Patent Application Ser. No. 62/558,113, filed on Sep. 13, 2017, of all of which being hereby incorporated entirely herein by reference.

BACKGROUND

Beetroot (also known as red beet or *Beta vulgaris*, but not to be confused with sugar beet) products have been very popular the latest years in part due to the surprising discovery that nitrate can reduce blood pressure, help maintain healthy blood pressure, improve athletic performance, reduce oxygen consumption, and generally help with general health, wellness and performance. Because beetroot is one of the vegetables containing the highest amount of nitrate (average range of 1459 [644-1800] mg/kg fresh weight and as high as 4500 mg/kg of dry weight), beetroot has been the prime candidate for the development of natural nitrate containing products that also comply with regulations established by the US Food and Drug Administration (FDA).

Advantages of using beetroot as a nitrate source include that it is a natural source and that beetroot can provide nitrate while complying with all standards and regulations established by the FDA and other health organization unlike artificial sources of nitrate like sodium nitrate. Another advantage is that beetroot can be available in "organic" form (according to the standards for "organic foods" established by the US Department of Agriculture (USDA) or other organic food standards) for people who are interested in natural, pesticide-free, and additive-free nitrate sources.

Studies on the health benefits of nitrate increasingly emerged in the past 10 years. According to the studies, the minimal dose of nitrate required to produce effects is about 50 mg; however, the majority of studies show more significant results starting at 150 mg with the recommended amount being around 322 mg nitrate/day. It is notable that most of the studies regarding the benefits of nitrate supplementation have been done on beetroot juice. Furthermore, and more importantly, beetroot juice high in nitrate supplementation has been shown to be superior to supplementation with sodium nitrate containing equimolar amount of nitrate for athletic performance as well as for blood pressure reduction.

Despite the many potential benefits of red beet supplementation, it has not been practical for daily supplementation with beetroot products. First, not every person is willing to eat beets every day. Second, many find the "earthy" taste of beetroot, which is due to geosmin found in beetroot, objectionable. Third, beets are naturally high in sugars, containing about 7 g sugars and a total of 10 g carbs per 100 g raw weight. More concentrated beet products, like beetroot juice or beetroot powder have even higher amounts of sugars, containing 9-10 g sugars per 100 ml. This can make consumption of beet products problematic for people who require low carbohydrate/sugar intake, such as diabetics or those looking to lose weight. Finally, the high carbohydrate content per dry weight of beetroot or beetroot powder also makes it difficult to make practical solid products, such as tablets, capsules or powder, that contain an efficacious dose of nitrate from beetroot juice.

All of the current beetroot dry products are either dried beetroot powder product or dried beet juice products. The content of nitrate in existing beetroot powder products is generally low, containing about 0.8 to a maximum of 2.5% of nitrate by weight. Because of the low content of nitrate in existing dried beetroot products, the vast majority does not even state the exact amount of nitrates contained in the product. Using Vernier's nitrate ion-selection electrode, the amount of nitrate in three popular powdered beetroot products marketed as "high in nitrate" actually only contained between 1% and 2.5% nitrate by weight.

Based on the concentration of nitrate in these "high in nitrate" dried beetroot products, it is very impractical to add efficacious amounts of beetroot in dry supplements/food products. To achieve the minimum studied dose of 157 mg nitrate, one would have to consume 15,700 mg or 15.7 g of powder (if the powder contained 1% nitrate), which at minimum would equal between 15 to 20 size 000 capsules. It is not surprising that no beetroot-based supplement to date can practically provide the efficacious dose of nitrate. Thus, the product labels falsely claim the benefits of nitrate administration while containing non-efficacious amounts. Accordingly, there is a long-felt need in the market for products made from beetroot higher in nitrate than 3%, which would allow for convenient administration of efficacious doses of nitrate.

SUMMARY

The disclosure encompasses methods of increasing nitrate content and reducing sugar content in dried beetroot product. The methods comprise mixing dried beetroot product with an extraction mixture comprising an alcohol and an acid, wherein the alcohol is a low molecular weight alcohol that is liquid at room temperature; steeping the mixture of the dried beetroot product and the extraction mixture to produce a steeped mixture; filtering the steeped mixture to produce a filtered product; and drying the filtered product to produce a dried filtered product. In some implementations of the method, the alcohol is selected from the group consisting of: ethanol, methanol, propanol, isopropanol, and isobutanol. In some implementations of the methods, the acid is selected from the group consisting of: acetic acid, formic acid, sulfuric acid, hydrochloric acid, nitric acid, hydrobromic acid, phosphoric acid, and perchloric acid. In one implementation, the ratio of the alcohol to acid in the extraction mixture is 3:1. In some embodiments, the extraction mixture is free of water. For example, the extraction mixture consists of absolute ethanol and glacial acetic acid.

In some aspects, the mixture of the dried beetroot product and the extraction mixture is steeped for 24 hours prior to the filtering step. In some implementations, steeping the mixture of the dried beetroot product and the extraction mixture further comprising stirring the mixture of the dried beetroot product and the extraction mixture.

In some implementations, the methods further comprise providing calcium hydroxide at a molar ratio of 2:1 to the acetic acid to the steeped mixture. In these implementations, the step of drying the filtered product does not exceed a temperature of 50° C. For example, drying the filtered product comprises air drying or high vacuum drying the filtered product, or drying the filtered product comprises high vacuum drying the filtered product at about 45° C.

The methods of increasing nitrate content and reducing sugar content in dried beetroot product may further comprise rehydrating the dried filtered product to produce a beetroot solution; adding an ethanol fermentation agent to the beetroot solution; fermenting the beetroot solution containing the ethanol fermentation agent, wherein sugars in the beetroot solution are converted into alcohol to produce fermented liquid; removing the alcohol from the fermented liquid to produce an enriched product; and filtering the fermented liquid or enriched product to remove the ethanol fermentation agent. The fermentation agent is selected from the group consisting of: baker's yeast, brewer's yeast, and *Zymomonas mobilis*. In some implementations, the filtered liquid is fermented at about 40° C.

In some embodiments, the methods further comprise heating the fermented liquid. In some aspects, removing alcohol from the fermented liquid comprises drying the fermented liquid after the ethanol fermentation agent is filtered from the fermented beetroot juice. In other aspects, removing alcohol from the fermented liquid comprises spray drying of the fermented liquid after the ethanol fermentation agent is filtered from the fermented liquid. In some implementations, fermenting the beetroot solution comprises stirring the beetroot solution containing the fermentation agent.

The disclosure also encompasses beetroot powder, wherein the beetroot powder comprises at least 3% by weight nitrate, for example, more than 4%, more than 5%, more than 6%, more than 7%, more than 8%, more than 9%, or more than 10% by weight nitrate. In some embodiments, the beetroot powder comprises less than 70% by weight sugar, for example, less than 65%, less than 60%, less than 55%, less than 50%, less than 45%, less than 40%, less than 35%, less than less 30%, less than 35%, less than 20%, less than 19%, less than 18%, less than 17%, less than 16%, or less than 15% by weight sugar. In some aspects, the beetroot powder is produced according to the methods of the disclosure.

DETAILED DESCRIPTION

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that implementations of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the concentrations provided in percentages are by weight.

As used herein, the term "about" refers to a deviation of no more than +/−10% of the given value.

As used herein, the term "baker's yeast" refers to the yeast strain or composition of yeast strains commonly used as a leavening agent in baking bread. Species of baker's yeast includes *Saccharomyces cerevisiae* and *Saccharomyces exiguus* (also known as *Saccharomyces minor*).

As used herein, the term "brewer's yeast" refers to the strain of yeast or composition of yeast strains commonly used in brewing. These include strains of S. *cerevisiae* and *Saccharomyces pastorianus* (formerly known as *Saccharomyces carlsbergensis*). In some implementations, brewer's yeast comprises the *Brettanomyces* and/or *Dekkera* genii of Saccharomycetaceae.

As referenced herein, the term "nitrate" refers only to the naturally occurring inorganic nitrate ($NO_3^-$) present in vegetables, such as beetroot. Accordingly, the amount or concentration of nitrate described herein do not refer to any contribution of nitrate content from other inorganic nitrate sources, such as potassium or sodium nitrate, that may be added to the natural product.

Unless specified otherwise, the description of percentages in relation to a composition refers to a percentage by weight.

The present disclosure addresses the need to create a beetroot powder product that contain at least 3% (by weight) nitrate, which allows for convenient daily administration of beetroot. The methods described herein both enriches typical beetroot powder to have higher nitrate content and reduces, if not removes, the sugar content in the beetroot powder. For example, the methods described herein increase nitrate content by at least three times, at least five times, at least ten times, at least 15 times, or at least 20 times greater than the conventional beetroot powder. Another benefit of enriching the beetroot powder according to the method of the present application is retaining the activity of temperature sensitive nutrients, like antioxidants such as betanin, as the process does not require heating above 50° C. In some aspects, the beetroot powder enriched according to the methods described herein increases the antioxidant content by at least 10%, for example, about 10%, about 15%, about 20%, or about 25%, as compared to the conventional beetroot powder. Although the methods of the invention may be practiced in conditions with a wide range of temperatures, room temperature is most preferable so that the antioxidants in the beetroot powder are best protected during the process. While performing the methods of the invention at higher temperatures may damage the antioxidant content of the beetroot powder, performing the methods of the invention at higher temperatures will still yield a product with higher nitrate and lower sugar content. The methods described herein may also be modified for similarly enriching the dried products of other high nitrate vegetables, such as carrots and radishes.

The methods of the disclosure comprises combining the dried beetroot product, such as beetroot powder, with an extraction mixture comprising an alcohol and an acid. In a preferred embodiment, the extraction mixture comprises alcohol and acid at a ratio of 3:1, or alternatively, 75% by volume alcohol and 25% by volume acid. Although different ratios of alcohol to acid will also produce products with higher nitrate and antioxidant content and lower sugar content than the original dried beetroot product, the ratio of 3:1 produced the most optimal results. Any low molecular weight alcohol that is liquid in room temperature, such as ethanol, methanol, propanol, isopropanol, or isobutanol, may be used as the alcohol in the methods of the invention. The acid of the extraction mixture may be any acid, organic or inorganic, that is liquid at room temperature and can be easily removed by evaporation or vacuum drying. For example, the acid in the extraction mixture may be acetic acid, formic acid, sulfuric acid, hydrochloric acid, nitric acid, hydrobromic acid, phosphoric acid, or perchloric acid. In a preferred embodiment, the extraction mixture comprises ethanol and acetic acid due to their low price, easy availability and suitability for use in food products. It is crucial for the optimal performance of the method that all reactants are as free from water as possible. Existence of water will increase the sugar content of the product while decreasing the nitrate content. Accordingly, the extraction mixture, if comprising ethanol and acetic acid, preferably is made by mixing absolute ethanol and glacial acetic acid. In some implementations, the extraction mixture consists of the alcohol and the acid.

After combining the dried beetroot product with the extraction mixture, the mixture is allowed to steep, for example, for 24 hours. The combination of the beetroot product and the extraction fixture is then filtered to collect the liquid, which in some embodiments is a bright red liquid. The liquid that passes through the filter is then dried with an air draft, preferably at a temperature below 50° C. The filtered product may be further dried to further remove any moisture. Any drying step of the methods of the present application preferably happens at a temperature less than 50° C., which avoids loss of antioxidants. Accordingly, the drying step may be performed via air drying or drying in a vacuum. For example, the filtered product may be dried under vacuum at about 49° C., about 48° C., about 47° C., about 46° C., about 45° C., about 40° C., about 37° C., about 35° C., about 30° C., about 25° C., about 22° C., about 20° C., about 17° C., or about 15° C. For drying in a higher vacuum (vacuum with pressure in the range from 100 mPa to 100 nPa is a high vacuum), the drying temperature can be even lower, as the boiling temperature of water in high vacuum can be below 0° C. At this stage, the dried filtered product lacks the characteristic earthy smell and taste of beetroot that can be tasted in the dried beetroot powder of the prior art. The dried filtered product also has increased nitrate content compared to the starting dried beetroot powder. In some implementations, the dried filtered product is ground into fine powder.

In preferred implementations, the combination of the dried beetroot product and the mixture of alcohol and acid is stirred during the steeping stage. Sedimentation and congregation of the dried beet product at the bottom of the vessel containing the extraction mixture will hinder the extraction process. Accordingly, for example, the extraction mixture is stirred while the dried beet product is gradually added into extraction mixture to avoid sedimentation and congregation of the dried beet product at the bottom of the vessel containing the extraction mixture. In such embodiments of the methods, the stirred combination is allowed to settled prior to filtering to allow improved removal of solids. In some implementations, the methods further comprise centrifuging the stirred extraction mixture to aid the removal of solids and improve separation of solids.

Because acetic acid has a much higher boiling point than ethanol, the methods of implementation may further comprise adding calcium hydroxide prior to the drying step. The addition of calcium hydroxide results in the formation of calcium acetate precipitate, which can be filtered out in the filtering step so that no acetate is found in the filtered liquid. The absence of acetate in the filtered liquid allows for drying the filtered liquid product at lower temperatures. In some aspects, the amount of calcium hydroxide added is a molar ratio of 2:1 calcium hydroxide to the amount of acetic acid in the extraction mixture. In some implementations, the calcium hydroxide is added to the steeped combination of the beetroot product and the extraction mixture prior to the step of filtering the combination. Accordingly, the solids removed in the filtering step includes the calcium acetate precipitates as well as solids from the beetroot product. In other implementations, the calcium hydroxide is added to the liquid from filtering the steeped combination of the beetroot product and the extraction mixture. After the addition of calcium hydroxide, the solution is filtered again to remove any precipitates formed from the addition of calcium hydroxide.

The dried filtered product may be further enriched to possess higher percentage of nitrate and reduced sugar level via ethanol fermentation. During ethanol fermentation, the sugars in the beetroot solution is converted into alcohol to produce fermented liquid. Accordingly, in some embodiments, the methods further comprise rehydrating the dried filtered product, for example with water, to produce a beetroot solution; fermenting the beetroot solution containing the fermentation agent to produce a fermented liquid; and removing alcohol from the fermented liquid to produce an enriched liquid.

The ethanol fermentation agent may be baker's yeast, brewer's yeast, or *Zymomonas mobilis*. In some implementations, the fermentation process comprises stirring or mixing the beetroot solution and the fermenting agent. For example, the mixture is gently stirred at 100 rpm. In some aspects, the fermentation process can take place at a temperature of at least room temperature, for example, at least 22° C., at least 25° C., at least 30° C., at least 35° C., at least 40° C. In some aspects, the fermentation process takes place at a temperature no higher than 45° C. or no higher than 40° C. In certain implementations, the fermentation process takes place at a temperature of between about 22° C. and about 30° C., for example, between about 22° C. and about 27° C., between about 22° C. and about 25° C., or about 25° C.

In some implementations, the alcohol is removed by evaporating the liquids of the fermented liquid, for example, by drying the fermented liquid. The preferred method of drying for commercial purposes is spray drying. The end result is enriched beetroot powder. Prior to spray drying, the ethanol fermentation agent is removed from the fermented beetroot juice, for example using a filter or by a centrifugation.

In other implementations, the alcohol is removed from the fermented liquid by fractional freezing. As water freezes at a lower temperature than ethanol, the liquid ethanol may be separated from the frozen water portion the fermented liquid (the enriched product). After fractional freezing to remove the ethanol, the enriched product can then be dried. In some implementations, the drying process includes evaporating the enriched product at about 60° C. or at less than about 50° C. In some implementations, the evaporation process may take place in a vacuum. In these implementations, the ethanol fermentation agent is removed before or after fractional freezing but prior to drying the enriched product to produce enriched and dried beetroot juice powder.

The present disclosure also encompasses beetroot powder that comprises at least 3% by weight nitrate, for example, more than 4%, more than 5%, more than 6%, more than 7%, more than 8%, more than 9%, or more than 10% by weight nitrate. In some embodiments, the beetroot powder comprises less than 70% by weight sugar, for example, less than 65%, less than 60%, less than 55%, less than 50%, less than 45%, less than 40%, less than 35%, less than less than 30%, less than 35%, less than 20%, less than 19%, less than 18%, less than 17%, less than 16%, less than 15%, less than 10%, or less than 5% by weight sugar. In some aspects, the beetroot powder is produced according to the methods described herein.

A person well versed in the art will understand that a variety of products can be made from the dried filtered product or enriched product prepared from the dried beetroot product. For example, the powder produced from drying the dried filtered product or enriched product may be made into tablets and other orally discrete dosage forms, such as capsules, cachets, pills, granules, pellets, beads, and particles. In some implementations, the tablets and other orally discrete dosage forms example, may optionally be coated with one or more enteric coatings, seal coatings, film coatings, barrier coatings, compress coatings, fast disintegrating coatings, or enzyme degradable coatings. Multiple coatings may be applied for desired performance.

Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi- particulate composition, a coated multi-particulate composition, an ion-exchange resin-based composition, an osmosis-based composition, or a biodegradable polymeric composition.

EXAMPLE 1:

The nitrate content of commercial USDA organic beetroot powder was analyzed using a Vernier Nitrate electrode. The content of nitrate (expressed as nitrate ion) was 0.98% by weight. The commercial USDA organic beetroot powder (50 g) was finely grounded using a mill and then gradually mixed with 500 ml of absolute ethanol/glacial acetic acid mixture. The absolute ethanol/glacial acetic acid mixture was made by mixing 375 ml of ethanol with 125 ml of glacial acetic acid. The composition of dried beet powder and absolute ethanol/glacial acetic acid mixture was allowed to steep with 24 hours with stirring. After 24 hours, the stirring was stopped, and the composition of dried beet powder and absolute ethanol/glacial acetic acid mixture was allowed to settle for 30 minutes prior to filtering. The filtered liquid product from the composition of dried beet powder and absolute ethanol/glacial acetic acid mixture was then air dried at 49° C. The resulting powder was further dried under high vacuum at 45° C. to remove any water residues. The powder also lacked the characteristic earthy smell and taste of beets from containing geosmin.

For analysis, one gram of the resulting product was dissolved in 100 ml of distilled water. The nitrate content assessed using the same Vernier probe and found to be 5.5%. The refractometer detected a sugar content of the dissolved powder (1 g powder in 10 ml water) was about 13%.

The remaining powder was reconstituted into liquid with 100 ml water. Two grams of brewer's yeast were added to the liquid, and the product was covered and left to ferment at room temperature. After 24 hours, the yeast was filtered out, and the liquid dried first with an air draft and then under high vacuum. The resulting bright red powder was again assessed with for sugar and nitrate content using the Vernier Nitrate electrode. Sugar content was found to be 0% while nitrate content was 7.5%.

EXAMPLE 2:

A commercial manufacturer prepared enriched beetroot extract from beet powder (produced from raw *Beta vulgaris*) according to the method of Example 1 herein. The enriched beetroot extract produced by the commercial manufacturer was analyzed for nitrate and sugar content and oxygen radical absorbance capacity (ORAC) value.

Using the Vernier Nitrate electrode, the nitrate content of the enriched beetroot content was 4.2% by weight.

According to the Certificate of Analysis from Eurofins Food Integrity & Innovation, the total amount of sugar in the enriched beetroot product is 55.3%, which is significantly less than sugar content of beetroot (between 80-90%). The sugar profile of the enriched beetroot extract is 0.6% fructose, 0.6% glucose, 54.1% sucrose, less than 0.1% lactose, less than 0.1% maltose, and less than 0.1% galactose.

According to the Certificate of Analysis from Eurofins Food Integrity & Innovation, the ORAC value is 179 μmol TE/g. This is more than 10 times higher than the ORAC value of raw beets. According to the USDA database for the ORAC values of selected foods, the ORAC value for raw beet is 1776 μmol TE/ 100 g, which is 17.76 μmol TE/g. In view of raw beets containing 87% water, the presumed ORAC value for beetroot powder produced by evaporating water from raw beets would be about 137 μmol TE/g. Thus, the method described herein increases the antioxidant concentration by about 25% in the enriched beetroot powder.

The invention claimed is:

1. A method of increasing nitrate content in a dried beetroot product, the method comprising:
    mixing the dried beetroot product with an extraction mixture comprising an alcohol and an acid, wherein the alcohol is a low molecular weight alcohol that is liquid at room temperature;
    steeping the mixture of the dried beetroot product and the extraction mixture to produce a steeped mixture;
    filtering the steeped mixture to produce a filtered product; and
    drying the filtered product to produce a dried filtered product, wherein the nitrate content of the dried filtered product is greater than the nitrate content of the dried beetroot product.

2. The method of claim 1, wherein the alcohol is selected from the group consisting of: ethanol, methanol, propanol, isopropanol, and isobutanol.

3. The method of claim 1, wherein the acid is selected from the group consisting of: acetic acid, formic acid, sulfuric acid, hydrochloric acid, nitric acid, hydrobromic acid, phosphoric acid, and perchloric acid.

4. The method of claim 1, wherein the ratio of the alcohol to the acid in the extraction mixture is 3:1.

5. The method of claim 1, wherein the extraction mixture is free of water.

6. The method of claim 5, wherein the extraction mixture consists of absolute ethanol and glacial acetic acid.

7. The method of claim 1, wherein the mixture of the dried beetroot product and the extraction mixture is steeped for 24 hours prior to the filtering step.

8. The method of claim 1, wherein steeping the mixture of the dried beetroot product and the extraction mixture further comprises stirring the mixture of the dried beetroot product and the extraction mixture.

9. The method of claim 1, further comprising providing calcium hydroxide at a molar ratio of 2:1 to the acid to the steeped mixture.

10. The method of claim 9, wherein the step of drying the filtered product is performed at a temperature not exceeding 50° C.

11. The method of claim 10, wherein drying the filtered product comprises
air drying, or
vacuum drying at a pressure between 100 mPa and 100 nPa.

12. The method of claim 11, wherein drying the filtered product comprises vacuum drying the filtered product at a pressure between 100 mPa and 100 nPa at about 45° C.

13. The method of claim 1, further comprising:
rehydrating the dried filtered product to produce a beetroot solution;
adding an ethanol fermentation agent to the beetroot solution;
fermenting the beetroot solution containing the ethanol fermentation agent, wherein sugars in the beetroot solution are converted into alcohol to produce fermented liquid;
removing the alcohol from the fermented liquid to produce an enriched product; and
filtering the fermented liquid or the enriched product to remove the ethanol fermentation agent.

14. The method of claim 13, further comprising heating the fermented liquid.

15. The method of claim 13, wherein removing alcohol from the fermented liquid comprises drying the fermented liquid after the ethanol fermentation agent is filtered from the fermented beetroot liquid or the enriched product.

16. The method of claim 13, wherein removing alcohol from the fermented liquid comprises spray drying of the fermented liquid after the ethanol fermentation agent is filtered from the fermented liquid or the enriched product.

17. The method of claim 13, wherein the fermentation agent is selected from the group consisting of: baker's yeast, brewer's yeast, and *Zymomonas mobilis*.

18. The method of claim 13, wherein fermenting the beetroot solution comprises stirring the beetroot solution containing the fermentation agent.

19. The method of claim 13, wherein the filtered liquid is fermented at about 40° C.

20. An enriched beetroot powder consisting essentially of a beetroot powder having an amount of beetroot-contributed inorganic nitrate ($NO_3^-$), wherein the amount of beetroot-contributed inorganic nitrate ($NO_3^-$) in the beetroot powder is at least 4% by weight of the enriched beet powder.

21. The enriched beetroot powder of claim 20, wherein the beetroot-contributed inorganic nitrate ($NO_3^-$) in the enriched beetroot powder is at least 5% by weight of the enriched beetroot powder.

22. The enriched beetroot powder of claim 20, wherein the beetroot-contributed inorganic nitrate ($NO_3^-$) in the enriched beetroot powder is at least 8% by weight of the enriched beetroot powder.

23. The enriched beetroot powder of claim 20, wherein the beetroot-contributed inorganic nitrate ($NO_3^-$) in the enriched beetroot powder is at least 10% by weight of the enriched beetroot powder.

24. The enriched beetroot powder of claim 20, wherein the beetroot-contributed inorganic nitrate ($NO_3^-$) in the enriched beetroot powder is between 4% by weight and 10% by weight of the enriched beetroot powder.

25. The enriched beetroot powder of claim 20, wherein the beetroot-contributed inorganic nitrate ($NO_3^-$) in the enriched beetroot powder is between 7% by weight and 10% by weight of the enriched beetroot powder.

26. An enriched beetroot powder, consisting essentially of a beetroot powder having an amount of beetroot contributed, inorganic nitrate ($NO_3^-$), wherein the amount of beetroot-contributed inorganic nitrate ($NO_3^-$) present in the enriched beetroot powder is at least 3% by weight of the enriched beet powder, and wherein the beetroot powder is produced according to a method comprising the steps of:
mixing a dried beetroot product with an extraction mixture comprising an alcohol and an acid, wherein the alcohol is a low molecular weight alcohol that is liquid at room temperature;
steeping the mixture of the dried beetroot product and the extraction mixture to produce a steeped mixture;
filtering the steeped mixture to produce a filtered product; and
drying the filtered product to produce a dried filtered product, wherein the nitrate content by weight of the dried filtered product is greater than the nitrate content by weight of the dried beetroot product.

27. An enriched beetroot powder consisting essentially of a beetroot powder having an amount of beetroot-contributed inorganic nitrate ($NO_3^-$) and, an amount of originally-occurring geosmin, wherein the amount of originally-occurring geosmin in the enriched beetroot powder is reduced by producing the enriched beetroot powder by a method comprising:
mixing a beetroot product with extraction mixture to form a beetroot product mixture; steeping the product mixture to produce a steeped mixture;
filtering the steeped mixture to produce a filtered product; and
drying the filtered product to produce an enriched, dried filtered product.

* * * * *